United States Patent [19]

Padmanathan

[11] Patent Number: 4,574,155

[45] Date of Patent: Mar. 4, 1986

[54] PROCESS FOR PREPARING 2-HYDRAZINO-1,3-DIAZACYCLOALK-2-ENE HYDROHALIDES

[75] Inventor: Thurairajah Padmanathan, Piscataway, N.J.

[73] Assignee: American Cyanamid Company, Stamford, Conn.

[21] Appl. No.: 587,414

[22] Filed: Mar. 8, 1984

[51] Int. Cl.$^4$ .................. C07D 239/02; C07D 109/04
[52] U.S. Cl. ................................ 544/330; 564/314
[58] Field of Search ..................... 544/330; 564/314

[56] References Cited

U.S. PATENT DOCUMENTS 2,525,927  10/1950  Mckay ........................... 544/298
4,258,181   3/1981  Murdock et al. ............... 544/296

FOREIGN PATENT DOCUMENTS 0050330  5/1975  Japan .............................. 564/314

OTHER PUBLICATIONS

Brugger et al., Justus Liebigs Ann. Chem. 764, 112–115, (1972).
Teulon et al., Chem. Abst. vol. 87, 152205e, 1977.
Heinemann, Chem. Abst. vol. 76, 122673m, 1972.
Brown et al., JCS 4044, (1962), pp. 4039–4045.
Finnegan et al., J. Org. Chem. 18, 779–790, 1953.
Mckay et al., JACS; 71, pp. 766–770, 1949.
Brugger et al., Chem. Abst. vol. 78, 84373v, 1973.

Primary Examiner—Donald G. Daus
Assistant Examiner—Cecilia Shen
Attorney, Agent, or Firm—Charles F. Costello, Jr.

[57] ABSTRACT

This invention provides a process for preparing a 2-hydrazino-1,3-diazacycloalk-2-ene hydrohalide. The process comprises reacting a one molar proportion of either tautomeric isomer of a 2-nitroamino-1,3-diazacycloalk-2-ene represented by the following formulas:

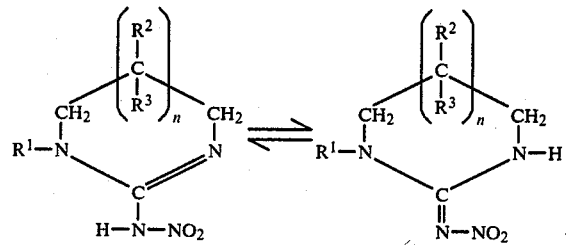

wherein $R^1$ is hydrogen, $C_1$–$C_6$ alkyl, $C_1$–$C_6$ hydroxyalkyl, $C_1$–$C_6$ alkoxyalkyl, phenyl, substituted phenyl, benzyl, or substituted benzyl, $R^2$ and $R^3$ are independently hydrogen, $C_1$–$C_6$ alkyl, $C_1$–$C_6$ alkoxy, $C_1$–$C_6$ alkoxyalkyl, hydroxyl, aryl, substituted aryl, aralkyl and substituted aralkyl, and n is an integer from 0 to 3 with about an equimolar proportion of an ammonium halide or hydrazonium halide, and about a 1 to 2 molar proportion of hydrazine hydrate in a composition selected from a $C_1$ to $C_4$ aliphatic alcohol, water or a mixture thereof, at a temperature from about ambient to the reflux, and isolating the end product as a monohydrohalide.

This invention also provides a process for preparing a 2-hydrazino-1,3-diazacycloalk-2-ene dihydrohalide. The process comprises reacting a compound of the formula:

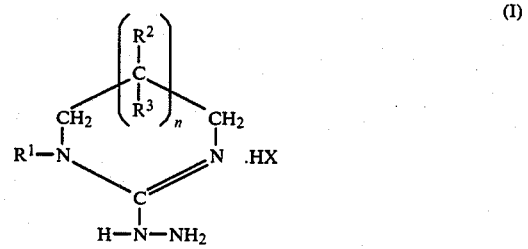

(I)

wherein $R^1$ is hydrogen, $C_1$ to $C_6$ alkyl, or $C_1$ to $C_6$ hydroxyalkyl, $R^2$ and $R^3$ are independently hydrogen or $C_1$ to $C_6$ alkyl, n is 0 to 3 and X is a halide ion, with hydrogen halide wherein the halide ion is the same as defined above in a $C_1$ to $C_4$ alkyl alcohol at about 0° to 30° C.; and recovering the corresponding 2-hydrazino-1,3-diazacycloalk-2-ene dihydrohalide.

16 Claims, No Drawings

PROCESS FOR PREPARING 2-HYDRAZINO-1,3-DIAZACYCLOALK-2-ENE HYDROHALIDES

The preparation of 2-hydrazino-1,3-diazacyclopent-2-ene hydroidide by reacting 2-methylthio-1,3-diazacyclopent-2-ene hydroiodide with hydrazine hydrate is disclosed by Finnegan et al, J. Org. Chem. 18, 779, 790 (1953). Subsequent reaction of the hydroiodide with hydrogen chloride affords 2-hydrazino-1,3-diazacyclopent-2-ene dihydrochloride, an intermediate for the preparation of bis(4,5-dihydro-1H-imidazol-2-ylhydrazone) of 9,10-anthracenedicarboxaldehyde dihydrochloride, an anticancer agent. However, this procedure involves the use of 2-imidazolidenethione, a known carcinogen, in the preparation of the 2-methylthio-1,3-diazacyclopent-2-ene hydroiodide, and the formation of environmentally undesirable methyl mercaptan when the latter is converted to 2-hydrazino-1,3-diazacyclopent-2-ene dihydrochloride. There is a need for a process for preparing 2-hydrazino-1,3-diazacycloalk-2-ene hydrohalides that will avoid the use of 2-imidazolidinethione and the production of undesirable mercaptan by-products.

Brown and Evans [J. Chem. Soc. 4044 (1962)] disclose the preparation of 2-amino-1,4,5,6-tetrahydropyrimidine hydrochloride by neat fusion of trimethylenediamine and guanidine hydrochloride at 140° C. for 3 hours. However, following this procedure the neat fusion of equimolar amounts of 2,2-dimethyl-1,3-diaminopropane and aminoguanidine hydrochloride at 140°–145° C. afforded a mixture of 2,2-hydrazino-5,5-dimethyl-1,3-diazacyclohex-2-ene monohydrochloride, and 1-amino-5,5-dimethyl-b 1,3-diazacyclohex-2-ene monohydrochloride in ratios from 2:1 to 5:1, depending on the length of the heating.

McKay et al [J. Am. Chem. Soc. 71, 766 (1949)] disclose the reaction of 2-nitroamino-1,3-diazacyclopent-2-ene, and 2-nitroamino-4-methyl-1,3-diazacyclopent-2-ene, with excess ethylenediamine at 80°–90° C. to prepare N-2-(1,3-diazacyclopent-2-ene)-ethylenediamine, and N-2-(4-methyl 1,3-diazacyclopent-2-ene)-ethylenediamine.

There is a need, however, for a process for preparing 2-hydrazino-1,3-diazacycloalk-2-ene hydrohalides that will provide high yields and high purity, while avoiding the formation of undesirable by-products.

SUMMARY OF THE INVENTION

This invention provides a process for preparing a 2-hydrazino-1,3-diazacycloalk-2-ene hydrohalide. These compounds, represented by formula (I), are tautomeric isomers of compounds of formula (IA)

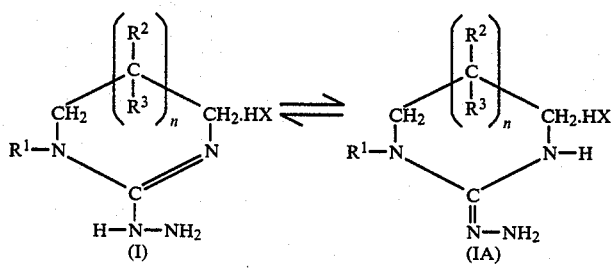

wherein $R^1$ is hydrogen, $C_1$-$C_6$ alkyl, $C_1$-$C_6$ hydroxyalkyl, $C_1$-$C_6$ alkoxyalkyl, phenyl, substituted phenyl, benzyl, or substituted benzyl, $R^2$ and $R^3$ are independently hydrogen, $C_1$-$C_6$ alkyl, $C_1$-$C_6$ alkoxy, $C_1$-$C_6$ alkoxyalkyl, hydroxyl, aryl, substituted aryl, aralkyl and substituted aralkyl, and n is an integer from 0 to 3.

The process of the present invention comprises reacting a one molar proportion of a 2-nitroamino-1,3-diazacycloalk-2-ene of formula (II), or its tautomeric form represented by formula (IIA),

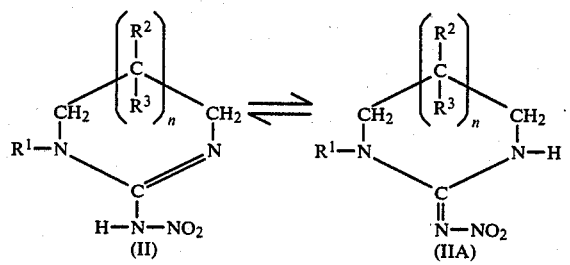

wherein $R^1$, $R^2$, $R^3$ and n are as defined above with about an equimolar proportion of an ammonium halide or hydrazonium halide, and with about a 1 to 2 molar proportion of hydrazine hydrate in a composition selected from a $C_1$ to $C_4$ aliphatic alcohol, water or a mixture thereof, at a temperature from about ambient to the reflux, and isolating the compound of formula (I).

In one embodiment, when n is zero $R^1$, $R^2$, and $R^3$ are hydrogen; in another embodiment when n is 1 $R^1$ is hydrogen, and $R^2$ and $R^3$ are methyl.

In yet another embodiment, the process comprises reacting formula (II) and hydrazine hydrate with a one molar proportion of an amine salt. The amine salt is selected from formula (III)

$$(R^4)_cN \cdot HX \qquad (III)$$

wherein $R^4$ is hydrogen or a $C_1$ to $C_4$ alkyl, and X is a halide or sulfate ion. In a specific embodiment, X is a chloride ion. In a more specific embodiment, the molar proportion of hydrazine hydrate is about 1.2 to 1.5. In a still more specific embodiment, the amine salt is ammonium chloride. In a most specific embodiment, the aliphatic alcohol is 1-propanol.

In a further embodiment, the reaction temperature for the process is from about 65° to 85° C. In a still further embodiment, the temperature is maintained for about 2 to 3 hours.

This invention also provides a process for preparing a 2-hydrazino-1,3-diazacycloalk-2-ene dihydrohalide. The process comprises reacting a compound of the formula

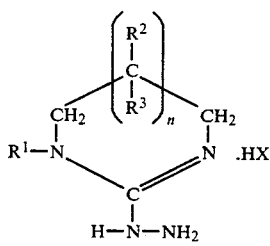

(I)

wherein $R^1$ is hydrogen, $C_1$ to $C_6$ alkyl, or $C_1$ to $C_6$ hydroxyalkyl, $R^2$ and $R^3$ are independently hydrogen or $C_1$ to $C_6$ alkyl, n is 0 to 3 and X is a halide ion, with hydrogen halide wherein the halide ion is the same as defined above in a $C_1$ to $C_4$ alkyl alcohol at about 0° to 30° C.; and recovering the corresponding 2-hydrazino-1,3-diazacycloalk-2-ene dihydrohalide.

In one embodiment, when n is 0 $R^1$, $R^2$ and $R^3$ are hydrogen, in another embodiment, when n is 1 $R^1$ is hydrogen and $R^2$ and $R^3$ are methyl.

In yet another embodiment, X is a chloride ion. In still another embodiment, the hydrogen halide is hydrogen chloride. In a final embodiment, the alkyl alcohol is 1-propanol.

DESCRIPTION OF PREFERRED EMBODIMENTS

In carrying out this invention, a stirred slurry, or solution, of a 2-nitroamino-1,3-diazacycloalk-2-ene of formula (II) or (IIA), containing about a one molecular proportion of an ammonium halide, or hydrazonium halide, and about 1–2 molecular proportions, preferably about 1.25–1.5 molecular proportions, of hydrazine hydrate per molecular proportion of 2-nitroamino-1,3-diazacycloalk-2-ene used, in a $C_1$–$C_4$ alcohol, or mixture of $C_1$–$C_4$ alcohols, preferably 1-propanol, is heated at reflux for about 2–24 hours, preferably about 2–3 hours. The reaction mixture is then cooled to crystallize the corresponding 2-hydrazino-1,3-diazacycloalk-2-ene monohydrohalide which is isolated by filtration or centrifugation. If the desired product does not crystallize, the reaction mixture is concentrated under vacuum to remove most of the solvent and the residue is treated with an appropriate solvent to induce crystallization. The wet cake is then dried under vacuum. The yield of 2-hydrazino-1,3-diazacycloalk-2-ene monohydrohalide obtained is about 70–95% of theoretical based on the 2-nitroamino-1,3-diazacycloalk-2-ene utilized. The product is about 95–100% pure.

Illustrative examples of suitable 2-nitroamino-1,3-diazacycloalk-2-ene compounds include the following:
2-nitroamino-1,3-diazacyclopent-2-ene,
5,5-dimethyl-2-nitroamino-1,3-diazacyclohex-2-ene,
3-methyl-2-nitroamino-1,3-diazacyclopent-2-ene,
2-nitroamino-5-propyl-1,3-diazacyclohex-2-ene,
3-ethyl-2-nitroamino-1,3-diazacyclopent-2-ene,
3-(2-hydroxyethyl)-2-nitroamino-1,3-diazacyclopent-2-ene,
2-nitroamino-1,3-diazacyclohept-2-ene,
2-nitroamino-1,3-diazacyclooct-2-ene,
and the like.

The above compounds can be prepared by methods disclosed by McKay and Wright in U.S. Pat. No. 2,525,927, and McKay, Bryce, and Rivington in Canadian J. Chem. 29, 382 (1951).

Illustrative examples of suitable ammonium halides and hydrazonium halides include the following:
ammonium chloride,
ammonium bromide,
ammonium iodide,
trimethylammonium chloride,
triethylammonium chloride,
hydrazine monohydrochloride,
hydrazine dihydrochloride,
and the like.

The following examples are illustrative of the processes of the present invention. All parts and percentages are by weight unless otherwise indicated.

EXAMPLE 1

Preparation of 2-Hydrazino-1,3-Diazacyclopent-2-ene Monohydrochloride

Hydrazine hydrate (78.4 grams; 1.566 moles) is added to a stirred mixture of 1-propanol (1420 mls), ammonium chloride (67.1 grams; 1.254 moles), and 2-nitroamino-1,3-diazacyclopent-2-ene (163.3 grams; 1.255 moles), over a period of 30 minutes, at 22°–26° C., in a well-ventilated hood. The resulting mixture is heated to 80° C. over a period of 1.5 hours, and stirred at 80°–81° C. for 2 hours. The reaction mixture is then slowly cooled to 0°–5° C., and stirred thereat for 30 minutes. The crystalline precipitate is isolated by filtration, washed with 1-propanol (2×120 mls), and dried under vacuum at 50° C. to obtain 131 grams (76% of theoretical) of the desired product, m.p. 181°–184° C.

EXAMPLE 2

Preparation of 2-Hydrazino-1,3-Diazacyclopent-2-ene Monohydroiodide

Hydrazine hydrate (6.75 grams; 0.135 mole) is added to a slurry of ethanol 2B (50 mls), ammonium iodide (14.5 grams; 0.1 mole), and 2-nitroamino-1,3-diazacyclopent-2-ene (13.0 grams; 0.1 mole) while allowing the temperature to rise to 32° C. The reaction mixture is stirred at 32° C. for 15 minutes, then heated to 75° C. over about 50 minutes and stirred thereat for 1.5 hours. The reaction mixture is allowed to cool to 40° C., over about precipitate is isolated by filtration, washed with ice cold ethanol 2B (10 mls) and dried in a vacuum oven at 50° C. There is obtained a white crystalline solid (7.33 grams; 32.1% of theoretical; m.p. 140°–142° C.), which has an infrared absorption spectrum identical to that of the desired product.

EXAMPLE 3

Preparation of 2-Hydrazino-5,5-Dimethyl-1,3-Diazacyclohex-2-ene Monohydrochloride Hydrazine hydrate (1.98 grams; 0.0396 mole) is added to a mixture of 1-propanol (50 mls), ammonium chloride (1.56 grams; 0.028 mole), and 2-nitroamino5,5-dimethyl-1,3-diazacyclohex-2-ene (5.0 grams; 0.029 mole). The resulting mixture is heated to 95° C. over a period of 20 minutes, and stirred thereat for 2 hours. Additional hydrazine hydrate (0.94 gram; 0.0187 mole) is then added to the reaction mixture, and heating at 95° C. is continued for an additional 24 hours. The slurry is then cooled to room temperature and the precipitate is isolated by filtration, washed with 1-propanol (20 mls) and dried under a vacuum at 50° C. to obtain 3.55 grams (68.5% of theoretical) of the desired product. Evaporation of the filtrate affords a second crop (1.5 grams) of the same compound. The total yield in two crops is 96.5% of theoretical. The infrared absorption spectra of the two crops are identical with that of 2-hydrazino-5,5-dimethyl-1,3-diazacyclohex-2ene monohydrochloride.

EXAMPLE 4

Preparation of 2-Hydrazino-1,3-Diazacyclopent-2-ene Dihydrochloride

Hydrazine hydrate (3.0 grams; 0.06 mole) in methanol (5 mls) is added at 20°-22° C. to a stirred mixture of methanol (25 mls), ammonium chloride (2.2 grams; 0.041 mole), and 2-nitroamino-1,3-diazacyclopent-2-ene (5.2 grams; 0.04 mole). The resulting mixture is heated to reflux (67° C.) and stirred at reflux for 4 hours. The solution is then cooled and transferred to a distillation flask (250 mls) with methanol (15 mls) and isopropanol (50 mls). The resulting solution is concentrated under vacuum to remove most of the solvent. The resulting solid residue is treated with isopropanol (25 mls), and the mixture is cooled to 0° C. and filtered to isolate a white solid. The solid is dried under vacuum to obtain 4.2 grams of 2-hydrazino-1,3-diazacyclopent-2-ene monohydrochloride. A second crop of 0.5 gram is obtained by further workup of the filtrate. The total yield in two crops is 86% of theoretical.

The solid of the first crop (4.2 grams; 0.0307 mole) is dissolved in methanol (84 mls), and cooled in an acetone-dry ice bath. Hydrogen chloride is then bubbled into the stirred solution for 5 minutes and the resulting precipitate is recovered by filtration, sucked dry, and dried under a vacuum at 40° C. to obtain 4.83 grams (90.8% of theoretical) of 2-hydrazino-1,3-diazacyclopent-2-ene dihydrochloride which is 99.3% pure.

EXAMPLE 5

Preparation of 2-Hydrazino-1,3-Diazacyclopent-2-ene Dihydrochloride

A stirred mixture of hydrazine hydrate (7.6 mls; 0.156 mole), 2-nitroamino-1,3-diazacyclopent-2-ene (16.25 grams; 0.128 mole), and ammonium chloride (6.7 grams; 0.125 mole) in 1-propanol (150 mls) is heated to 78°-80° C. and maintained thereat for 3 hours. The excess hydrazine hydrate and solvent are then evaporated from the mixture under vacuum and the residual solid is treated with fresh 1-propanol (200 mls). The resulting slurry is cooled to 5° C., and gaseous hydrogen chloride is bubbled into it for 25 minutes, while stirring and maintaining the temperature below 10° C. The solid is then isolated by filtration, washed with 1-propanol (50 mls), and dried in a vacuum oven to obtain 20.6 grams (95% of theoretical) of crystalline solid (m.p. 182°-184° C.), which is identified as the desired product by its infrared absorption spectrum.

EXAMPLE 6

Preparation of 3-Ethyl-2-Hydrazino-1,3-Diazacyclopent-2-ene Monohydrochloride

Hydrazine hydrate (7.5 grams; 0.15 mole) in 1-propanol (10 mls) is added to a stirred mixture of ammonium chloride (5.4 grams; 0.10 mole), 3-ethyl-2-nitroamino-1,3-diazacyclopent-2-ene (15.8 grams; 0.10 mole), and 1-propanol (70 mls) at 20°-25° C. The resulting mixture is heated to 80° C. over a period of 0.5 hour and stirred at 80° C. for 1.5 hours. The reaction mixture is then heated to 92° C., held thereat for 3 hours, and then treated with additional hydrazine hydrate (0.5 gram; 0.01 mole). Stirring at 92° C. is continued for an additional 1.5 hours and the reaction mixture is allowed to cool to ambient temperature. The reaction mixture is then filtered to remove insoluble material and the filtrate is concentrated under vacuum to remove solvent and obtain a solid residue. The hygroscopic residue is dried under vacuum at 50° C. to obtain 15.7 grams (95.4% of theoretical) of the desired product, m.p. 80°-83° C.

EXAMPLE 7

Preparation of 3-Ethyl-2-Hydrazino-1,3-Diazacyclopent-2-ene Dihydrochloride

A portion of the product of Example 6 (10.0 grams; 0.06 mole) is dissolved in 1-propanol (65 mls), and the solution is cooled to 5° C. Gaseous hydrogen chloride is then bubbled into the reaction mixture for 10 minutes while stirring and maintaining the temperature below 25° C. The reaction mixture is then cooled to 10° C. and the colorless crystals which separate are isolated by filtration, washed with ice cold 1-propanol, and dried under vacuum at 50° C. to obtain 11.03 grams (86% of theoretical) of the desired product, m.p. 158° to 161° C. (dec.).

I claim:

1. A process for preparing a compound of formula (I)

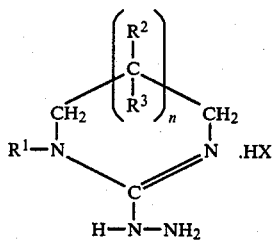

(I)

wherein $R^1$ is hydrogen, $C_1$-$C_6$ alkyl, $C_1$-$C_6$ hydroxyalkyl, $C_1$-$C_6$ alkoxyalkyl, phenyl, substituted phenyl, benzyl, or substituted benzyl, $R^2$ and $R^3$ are independently hydrogen, $C_1$-$C_6$ alkyl, $C_1$-$C_6$ alkoxy, $C_1$-$C_6$ alkoxyalkyl, hydroxyl, phenyl, substituted phenyl, benzyl and substituted benzyl, with the proviso that none of the substituted radicals contain a halo, sulfidyl, nitro or ring keto group, and n is an integer from 0 to 3, comprising:

reacting a one molar proportion of a compound of formula (II)

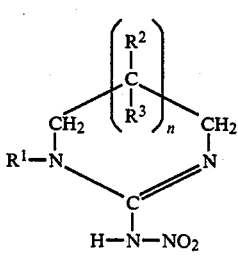

(II)

wherein $R^1$, $R^2$, $R^3$ and n are as defined above with about an equimolar proportion of an ammonium halide or hydrazonium halide, and about 1 to 2 molar proportions of hydrazine hydrate in a composition selected from a $C_1$ to $C_4$ aliphatic alcohol, water or a mixture thereof, at a temperature from about ambient to the reflux, and isolating the compound of formula (I).

2. A process of claim 1 wherein $R^1$, $R^2$ and $R^3$ are hydrogen and n is zero.

3. A process of claim 1 wherein $R^1$ is hydrogen, $R^2$ and $R^3$ are methyl and n is 1.

4. A process according to claims 1, 2 or 3 wherein in the reacting step said formula (II) and hydrazine hydrate is reacted with a one molar proportion of an amine salt, said salt selected from formula (III)

$$(R^4)_3N.HX \qquad (III)$$

wherein $R^4$ is hydrogen or $C_1-C_4$ alkyl and X is a halogen or sulfate.

5. A process according to claim 4 wherein X is chloride.

6. A process according to claim 5 wherein the molar proportion of hydrazine hydrate is about 1.2 to 1.5.

7. A process according to claims 4, 5 or 6 wherein said amine salt is ammonium chloride.

8. A process according to claims 4, 5, 6 or 7 wherein said aliphatic alcohol is 1-propanol.

9. A process according to claim 8 wherein said reaction temperature is from about 65° to 85° C.

10. A process of claim 9 wherein said temperature is maintained for about 2 to 3 hours.

11. A process for preparing a 2-hydrazino-1,3-diazacycloalk-2-ene dihydrohalide comprising: reacting a compound of the formula

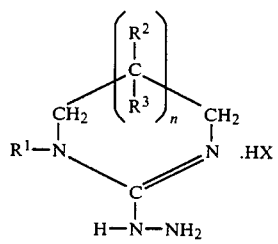

wherein $R^1$ is hydrogen, $C_1-C_6$ alkyl, or $C_1-C_6$ hydroxyalkyl, $R^2$ and $R^3$ are independently hydrogen or $C_1-C_6$ alkyl, n is 0 to 3 and X is a halide ion, with hydrogen halide wherein the halide ion is the same as defined above in a $C_1-C_4$ alkyl alcohol at about 0° to 30° C.; and recovering the corresponding 2-hydrazino-1,3-diazacycloalk-2-ene dihydrohalide.

12. A process of claim 11 wherein $R^1$, $R^2$ and $R^3$ are hydrogen and n is zero.

13. A process of claim 11 wherein $R^1$ is hydrogen, $R^2$ and $R^3$ are methyl and n is 1.

14. A process of claim 12 or 13 wherein X is a chloride ion.

15. A process of claim 14 wherein said hydrogen halide is hydrogen chloride.

16. A process of claim 14 or 15 wherein said alcohol is 1-propanol.

* * * * *